United States Patent [19]
Sitte

[11] 4,302,950
[45] Dec. 1, 1981

[54] DEVICE FOR METALLIC MIRROR-CRYOFIXATION AND SUBSEQUENT CRYOPREPARATION OF BIOLOGICAL MATERIALS

[75] Inventor: Hellmuth Sitte, Seefeld, Austria

[73] Assignee: C. Reichert Optische Werke, AG, Vienna, Austria

[21] Appl. No.: 185,631

[22] Filed: Sep. 9, 1980

[30] Foreign Application Priority Data

Nov. 6, 1979 [DE] Fed. Rep. of Germany ....... 2944806

[51] Int. Cl.³ ............................................. F25B 19/00
[52] U.S. Cl. ...................................... 62/514 R; 62/78
[58] Field of Search .......................... 62/78, 45, 514 R

[56] References Cited

U.S. PATENT DOCUMENTS

3,406,531 10/1968 Swenson et al. ......................... 62/78
3,662,566 5/1972 Brand ................................. 62/514 R
3,978,686 9/1976 Lechner et al. .................... 62/514 R

FOREIGN PATENT DOCUMENTS

2906153 11/1980 Fed. Rep. of Germany .

OTHER PUBLICATIONS

Sitte; H. et al., "Fast Freezing Device", *Journal of Microscopy*, vol. III, Pt 1, 9/1977, pp. 35–38.

Primary Examiner—Ronald C. Capossela
Attorney, Agent, or Firm—Alan H. Spencer

[57] ABSTRACT

The invention concerns a device for metallic mirror-cryofixation and subsequent cryopreparation of biological materials for microscopic, in particular electron microscopic examinations, employing a highly polished metallic mirror cooled to very low temperatures by a cryogen and mounted in a metal freezing chamber, which can be flooded with a gaseous cryogen, on which an object can be placed by means of an injection mechanism or the like, wherein the freezing chamber has an adequate volume for cryopreparation and for accepting the required accessory devices.

5 Claims, 9 Drawing Figures

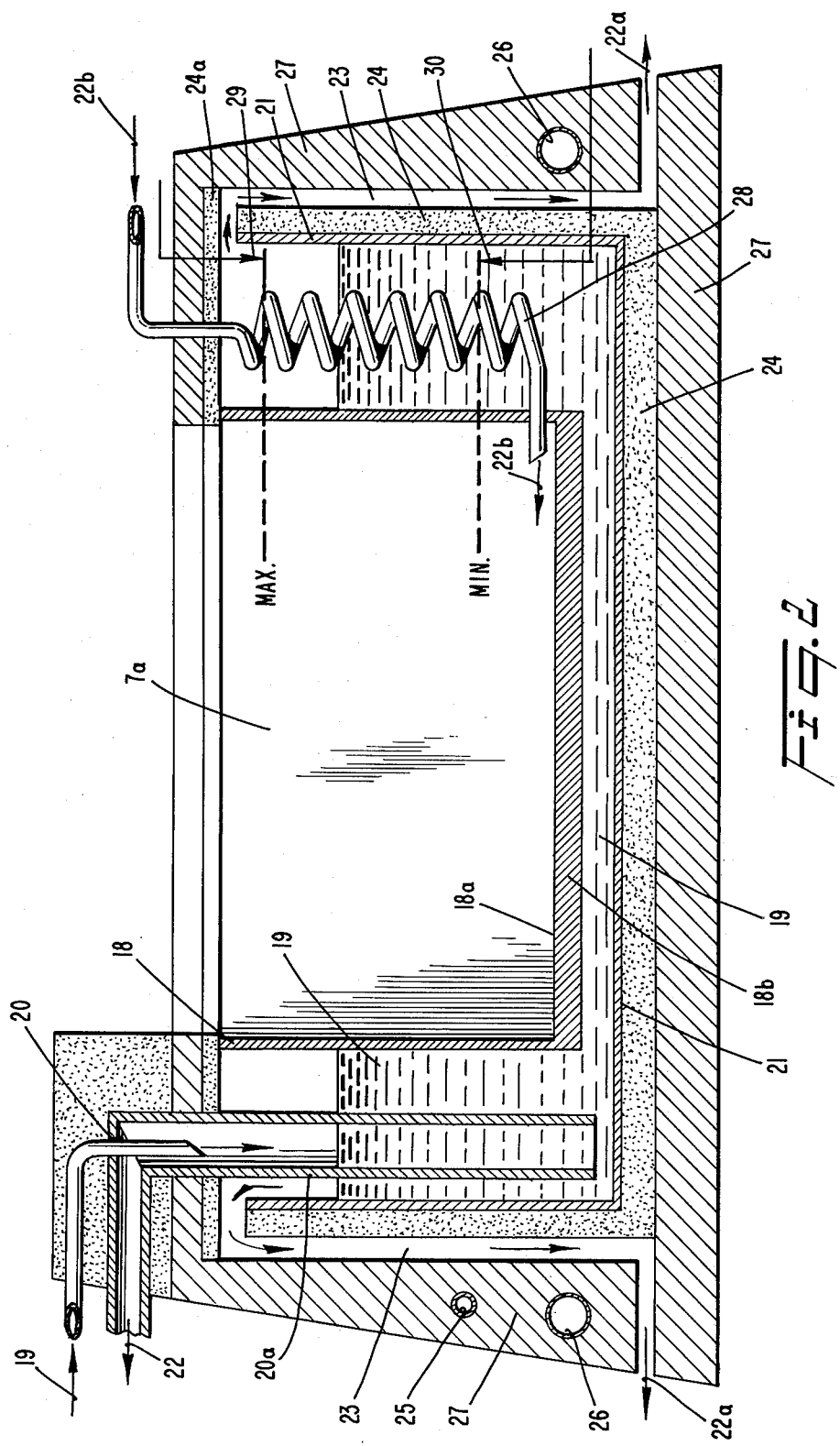

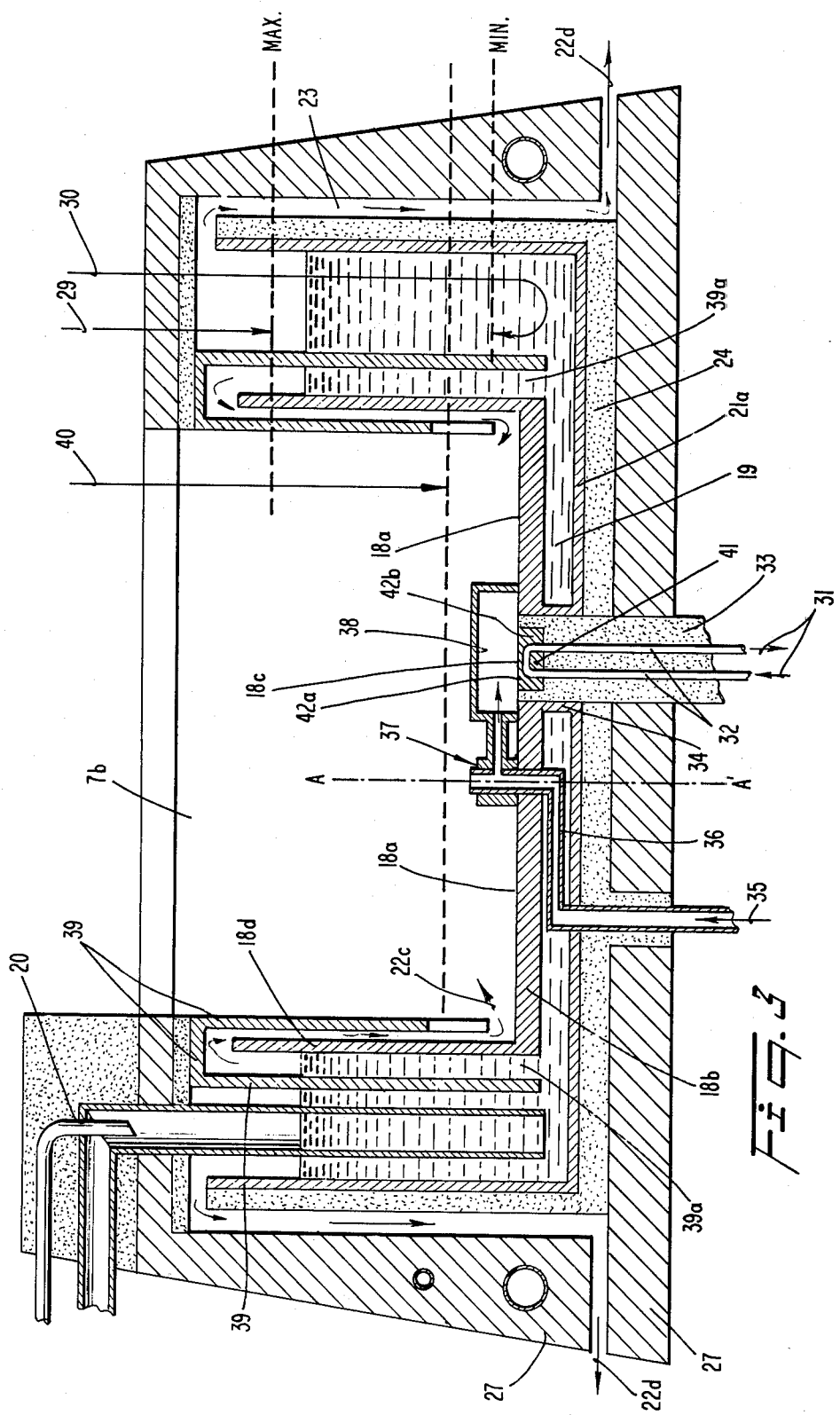

DEVICE FOR METALLIC MIRROR-CRYOFIXATION AND SUBSEQUENT CRYOPREPARATION OF BIOLOGICAL MATERIALS

BACKGROUND OF THE INVENTION

In the cryopreparation of biological materials for microscopic, especially electron microscopic examinations, preparation chambers with a volume of more than 1 l are being used with increasing frequency; in these chambers both the specimens and the necessary tools may be kept reproducibly at very low temperatures without icing up due to the condensation of atmospheric moisture. An important aid employed in the cryofixation of biological materials is a highly polished metallic surface ("metallic mirror") which is cooled to temperatures of less than 100° K. by means of a suitable cryogen and on which the biological object of interest is placed by means of a precisely controlled, high-speed injector. Immediately after the object surface strikes the metallic mirror, a marginal area of the object about 10 to 20 um wide is frozen within an extremely short time by direct thermal contact with the metallic mirror at a cooling rate of more than 1,000° C./second. In contrast to the freezing of the adjacent, deeper zones of the specimen, those which are more than 10 to 20 um removed from the marginal and "metal/object" contact zone, the marginal zone freezes rapidly (cryofixation by means of thermal shock); there is no separation detectable with the electron microscope of the aqueous, plasmatic, mixed phases which form the matrix of biological materials, whereas the deeper regions, due to the lower cooling rates of less than 1,000° C./second occurring in them, exhibit separation phenomena which are characterized by the occurrence of ice crystals inside the cells and in the intercellular spaces. Since these ice crystals, as artificial products ("artefacts") rule out any meaningful examination of the microstructure or ultrastructure, one strives to keep the temperature difference between the normal temperature of the living object (e.g., 37° C. in warm-blooded animals) and the freezing surface of the metallic mirror as large as possible in order to preserve the deepest possible marginal area of the specimen in a true-to-life state, i.e., without ice crystal artefacts, by means of the steepest possible temperature gradient. Thus, it is an obvious step to cool the metallic mirror by means of a cryogen whose temperature lies below the boiling temperature of liquid $N_2(-196°$ C.). To achieve this result either partially solidified nitrogen ("nitrogen slush", which has the melting temperature of |solid| nitrogen, $-210°$ C.) or liquid helium (minimum temperature at the condensation point: about 4° K.) may be used.

A device for metallic mirror-cryofixation is known in which a freezing chamber having a volume of less than 100 ml is used; its floor is formed by the highly polished upper surface of a massive block of silver. The silver block is immersed in nitrogen slush which is contained in a Dewar vessel and reaches a temperature of less than $-200°$ C. In order to prevent condensation of atmospheric nitrogen on the metallic mirror, this freezing chamber may be flushed with circulating helium gas which is passed through the nitrogen slush in the Dewar before entering the freezing chamber and is therefore pre-chilled to a temperature which corresponds approximately to that of the silver mirror (see *Journal of Microscopy*, Vol. 111, Part 1, pp. 35–38, September, 1977). Because of the small volume of its freezing chamber, cryopreparation is not feasible with this known device.

PRIOR ART

In contrast to the system described above, a device of the type cited at the outset, reflecting a prior proposal of the applicant (No. P 29 06 153.8) exhibits a large volume of more than 1 l. In this version, both the floor as well as the side walls of the chamber are made of metal and a minimum of two of the side walls, or alternatively all the side walls and the floor of the chamber, are cooled with a liquid cryogen, preferably liquid nitrogen (liquid $N_2$). In this system, provided that one foregoes partial solidification of the liquid $N_2$ and the associated relatively slight reduction in temperature of 14° C. from $-196°$ to $-210°$ C., a flushing system that is relatively simple to construct suffices: it uses pre-chilled dry nitrogen gas which may, for example, be introduced via a tube that first passes through the liquid $N_2$ used to cool the metal walls of the chamber.

According to the state of the art, freezing chamber of the previously described type have devices which, for example, make it possible to produce a freshly sectioned plane on the biological object of interest immediately before it is injected into the freezing chamber and consequently before its cryofixation on the very low temperature metallic mirror. As a result, the fresh plane surface of the object can be shock-frozen without artefacts and can be displayed in this condition for light or electron microscopy.

SUMMARY OF THE INVENTION

The highly desirable and often attempted cooling of a metallic mirror by means of liquid helium to temperatures of approximately 20° K. or less has been hindered by technical problems and by the immense costs involved. For example, attempts have been made to flush small freezing chambers having volumes of less than 100 ml so forcefully with helium gas that in spite of the extremely low temperatures on the metallic mirror, no gas from the ambient atmosphere, especially no solid nitrogen, condenses. But, when larger preparation chambers with volumes >1 l are used, especially when the preparation work usually required for methodological reasons must be done with the freezing chamber open, this procedure becomes impractical because of the high cost of helium gas. For the same reason, it is practically impossible to cool larger metallic mirror surfaces, let alone the metallic walls of freezing chambers having volumes on the order of 1 l or more, by using liquified helium. Attempts undertaken very recently to house the surface of a metallic mirror cooled by liquid helium in a vacuum pose the requirement that the biological objects to be examined must first be introduced into the vacuum by means of a suitable air-lock system. And even though the design of such air-lock systems is known from the technology used in electron microscopes, in this context, the associated costs appear pointless because it is precisely those marginal areas, 10 to a maximum of 20 um deep, capable of being frozen during cryofixation of a biological specimen which has a high water content, that are immediately and extremely altered in the high vacuum required with this method. Consequently, according to the state of the art, the problem of fixation at very low temperatures does not appear to be satisfactorily solved either from the standpoint of constructing the apparatus or with respect to the enormous costs associated with a helium cooling system. For these reasons, routine use of a helium cooling system is ruled out given the current state of the art.

Therefore, the objective of the present invention is to realize a freezing chamber of the type described at the outset which does not exhibit the aforesaid deficiencies and limitations and which thus makes it possible, at acceptable cost, to cool the metallic mirror surface required for cryofixation and having, for example, a size of between 1 and 10 cm$^2$ to temperatures $\leq 20°$ K. using liquid helium, without causing condensates, especially of solid nitrogen, to form on the metallic mirror before the object is placed on it and without limiting the chamber space required for subsequent cryopreparation to volumes of less than 1 l or the cold floor area required for cryopreparation to an area of less than 50 cm$^2$, for example, because condensates of the described type diminish the results of cryofixation or render them worthless.

According to the invention and by proceeding from the device described in the prior proposal of the applicant, this problem is solved by the fact that the metallic mirror has a zone of small surface area which is thermally isolated from the rest of the mirror surface; this small area can be covered by a movable lid which, along with the mirror area, encloses a hollow interior space, and it can be separately cooled by means of liquid helium, while the interior space can be separately flushed with cold helium gas.

Thus, in contrast to the state of the art, the highly polished surface of the metal chamber floor consists of two sections which are, to a large extent, thermally isolated from one another and which lie preferably in the same plane; of these, one small section having a surface area between 1 and 10 cm$^2$ is cooled with liquid helium to a temperature of $\leq 20°$ K. and a larger section having a surface area $\geq 50$ cm$^2$ is cooled with a higher temperature cryogen, preferably liquid $N_2$, to a temperature of $\leq 100°$ K. Solid or liquid condensates on these metallic mirror surfaces are prevented by flushing with suitable, pre-cooled protective gases in each case: for example, by separately flushing the liquid helium-cooled smaller surface with He gas and the larger, liquid nitrogen-cooled surface with $N_2$ gas. Here, effective flushing of the smaller, very low temperature, metallic mirror surface with protective He gas is achieved by using minimal quantities of helium since, during the entire cool-down phase until immediately before injection of the object, this surface is kept covered with a lid which has low heat capacity and low mass. The bottom surface of this lid has a recess through which the cooled helium gas enters and whose edges lie so close to the very low temperature area or the adjacent area that the helium vents through a small gap between the lid and the mirror surface which has a total cross-section of less than 10 mm$^2$. In this case a very low flow rate of helium gas on the order of less than 10 ml/min is sufficient to eliminate completely any $N_2$ flushing gas from the chamber diffusing in over the helium-cooled, very low temperature surface. The described flushing of the very low temperature surface with protective helium gas is not interrupted until immediately before the biological sample is placed on this section of the metallic mirror by swinging aside the lid.

Compared with the metallic mirror and cryopreparation systems known to date, the invented device has a number of important advantages: expensive helium cooling remains restricted to a small, largely thermally isolated part of the metallic mirror surface and for this reason functions with a minimum cryogen or cooling expenditure, while the helium used for cooling can be recycled using a known process and thus is not lost. By separately flushing this portion of the metallic mirror with protective helium gas, it is possible, as a result of the special covering system, to make do with a very low flow rate of helium gas. This appears to be especially important because the protective gas used for flushing cannot be recovered in a recycling system. Finally, this approach prevents exposure of the specimen to physicochemical effects, in particular to a hard vacuum, which damage irreversibly precisely those marginal areas that are accessible during cryofixation for microscopic or electron microscopic examination and which prolong the duration of the preparation process, after a freshly sectioned surface has been readied, in an equally damaging manner. On the contrary, without additional features—such as a hard vacuum system with suitable pumps, valves, vacuum gauges, and air-locks, which also increases equipment costs considerably, prolongs the preparation process in an unreasonable manner, and thus does not insure that a marginal area free from artefacts will be achieved—after a freshly sectioned surface is prepared and mounted in the injector, the object can be placed on the metallic mirror within fractions of a second.

An advantageous elaboration of the invention provides that the larger section of the metallic mirror, like the chamber as a whole, is flushed with nitrogen gas in a simple and effective manner by means of metal deflectors which divert one part of the $N_2$ gas that is continuously being formed during cooling of the metal chamber onto the chamber floor. The resulting laminar flow of nitrogen gas flushing the chamber prevents any ice build up in the freezing chamber in a very simple way without additional expensive techniques, even when operations are carried out with the chamber completely open. If required, in a further elaboration of this principle, the flow of nitrogen through the freezing chamber can be smoothly increased by means of one or more heating elements which evaporate additional $N_2$ gas and direct it toward the deflectors.

Another advantageous elaboration of the invention may consist in the fact that immediately after the specimen is placed on the very low temperature metallic mirror, i.e., the separate area of the mirror—in an operation suitably coordinated with the injection process, as required, and with any other requirement by raising the level of liquid $N_2$ in the surrounding $LN_2$ container—the chamber space is filled with liquid $N_2$ from the cooling tank so that extremely rapid and complete cooling of the sample takes place and so that an extremely low temperature, coming very close to the boiling point of liquid $N_2$, is attained for cryopreparation.

BRIEF DESCRIPTION OF THE DRAWINGS

Additional advantages and features (of the invention) will emerge from the following description of preferred exemplary embodiments with the aid of the attached drawings as well as from the additional subclaims. Shown in the drawings are:

FIG. 2 is a schematic section through a freezing chamber according to the prior proposal No. P 29 06

Figure 1:
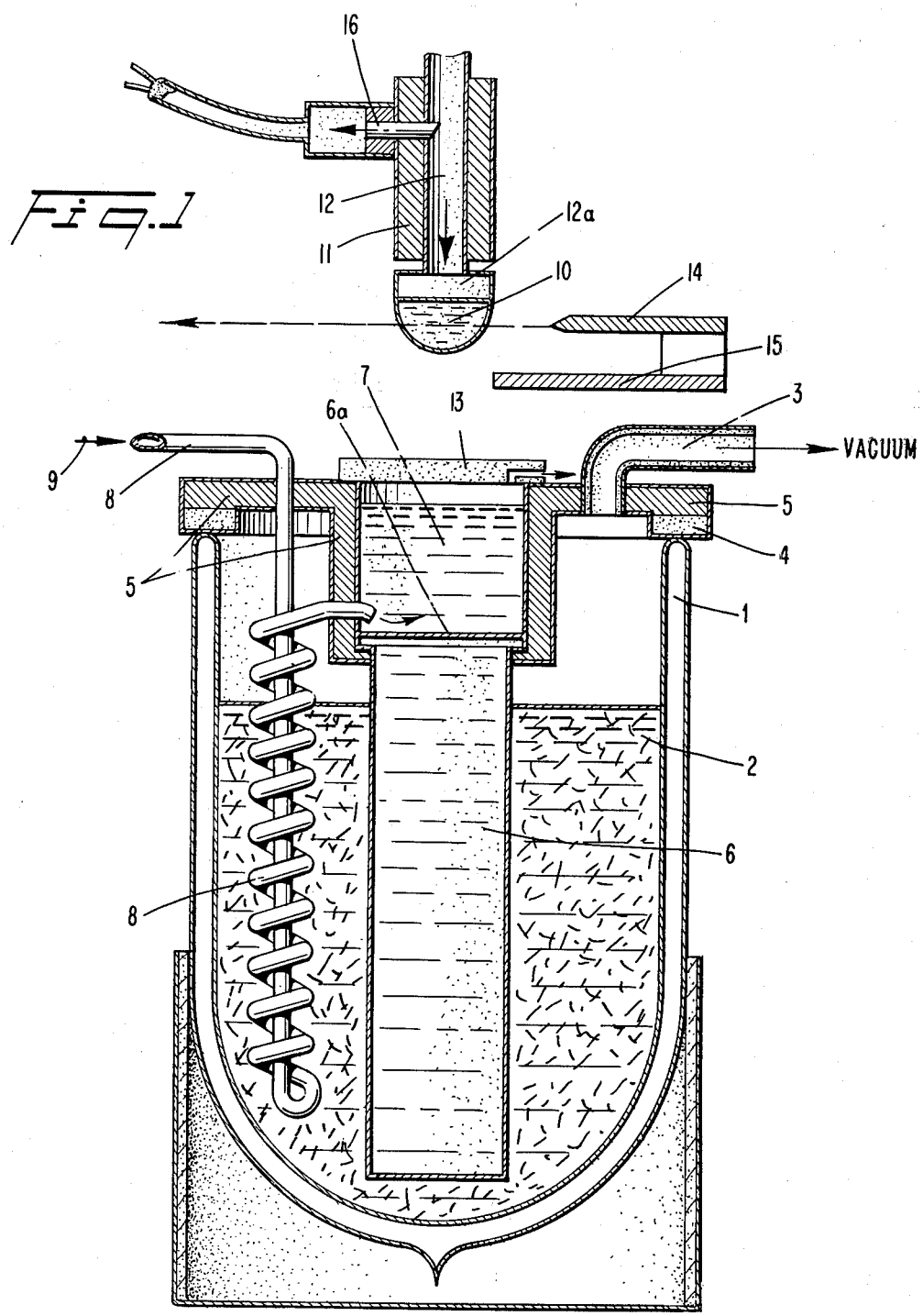
FIG. 1 is a schematic section through a small freezing chamber of conventional design incorporating a metallic mirror and an injection system for cyofixation.

153.8 employing a larger volume, liquid N$_2$ refilling via a phase separator, and protective gas flushing—shown in a simplified illustration which omits the injection system of FIG. 1;

FIG. 3 is a schematic section through the freezing chamber of a device designed according to the invention and having two separate metallic mirror surfaces at different temperatures, separate protective gas flushing systems for the separate freezing zones, and rapid, liquid N$_2$ cooling in the chamber space; and FIG. 4 is a comparison of various solutions (a) through (f) for thermally isolating the two metallic mirror surfaces at different temperatures, shown in schematic section.

THE PREFERRED EMBODIMENTS

The construction of the small freezing chamber for metallic mirror-cryofixation illustrated diagrammatically in FIG. 1 is of conventional design: the nitrogen 2 contained in the Dewar vessel 1 is partially solidified by being connected to a vacuum system at the coupling 3 of the lid 5 which rests on a gasket 4 and thus has a temperature of −210° C. Consequently, the upper surface 6a ("metallic mirror") of the highly polished silver cylinder 6 reaches a temperature of less than −200° C. To prevent condensates or sublimates from forming on the mirror surface 6a, a small freezing chamber 7 is continuously flushed with helium gas 9 via the tube 8. The plunger 12 running in a precisely cylindrical guide 11 serves in inject the specimen 10. On the bottom surface 12a of the plunger 12, the specimen may be held in a simple manner, for example, by a suction device which is not shown. Until the specimen 10 is injected, the freezing chamber 7 remains closed by a lid 13. Before injection, a freshly sectioned surface parallel to the metallic mirror 6a can be produced on the object 10 by means of a special knife 14, moved in the direction of the arrow. Here the bottom part 15 of the knife holder receives the portion cut off of the specimen 10. After the cutting procedure is concluded, the knife holder 14/15, which moved to the left, automatically releases the locking pawl 16 and thus initiates the injection process with the plunger 12/12a carrying the specimen 10 (in the direction of the arrow). A similar coordinate operation causes the freezing chamber 7 to open at the proper time by withdrawing the lid 13. The freshly sectioned surface of the object 10 produced by the special knife 14 contacts the very low temperature metallic mirror 6a approximately 0.1 second after it has been cut. The principal drawback of this system as shown in FIG. 1 consists in the fact that because of the small volume of the freezing chamber 7, it is not possible to remove excess material containing ice crystal artefacts after cryofixation has been completed. Cryotransfer results in equally serious difficulties, because most of the chamber floor, i.e., metallic mirror 6a, is covered by the specimen 10 and consequently, the specimen cannot be removed from the freezing chamber 7 without the risk of warming up the cryofixed surface and the formation of ice condensates. Since freezing the specimen 10 completely through in the freezing chamber 7 requires some time, it is thus also impossible to process several specimens in rapid sequence using this method.

These problems with the system shown in FIG. 1 can be partially eliminated by the device shown in FIG. 2; it has a freezing chamber 7a with a volume $\geq 1 l$. The walls of this freezing chamber 7a consist of sheet metal 18 throughout, while the floor 18b is finished as a highly polished mirror surface 18a for cryofixation and cryopreparation. Liquid N$_2$, preferred for cooling, is fed into a sheet metal tank 21 via the phase separator 20; the tank 21 surrounds the freezing chamber 7a so that the metal walls 18/18b of the freezing chamber are cooled directly by the liquid nitrogen. During filling, an immersion tube 20a of the phase separator 20 causes gaseous nitrogen 22 to be separated immediately from liquid nitrogen 19; in this sense immersion tube 20a functions like a conventional trap in a waste line. Nitrogen gas 22a, which is continuously evaporating from the metal tank 21 vents through a gap 23 between the insulation 24/24a and the metal jacket 27. The metal jacket 27 is heated thermostatically be means of a temperature sensor 25 and a cartridge heater 26, so that the gas 22a is heated to room temperature. The freezing chamber 7a may be flushed with dry nitrogen gas that is pre-cooled in a tube system 28 running through the liquid nitrogen 19 which bathes the freezing chamber. By means of two level sensors 29/30, in conjunction with a refilling system of known design which is not illustrated, the level of liquid N$_2$ in the tank 21 may be consistently and automatically maintained at a given level (see "min" and "max" data in FIG. 2). The described freezing chamber 7a makes possible cryofixations and cryopreparations at chamber temperatures of less than −150° C., while due to the large volume of the freezing chamber the most varied preparations can be accomplished side by side and cryofixations can be performed rapidly one after the other. For this, the cryofixed specimens are transferred immediately after they have been injected to another area of the large metallic mirror 18a without risk. Nevertheless, in this system work at temperatures below −210° C., which requires helium cooling, entails immense costs, since the cooling and flushing of the chamber require very large quantities of helium or refrigeration capacity.

As shown in FIG. 3, the freezing chamber designed according to the invention and conforming in its basic principle to FIG. 2 makes possible helium cooling and flushing with helium gas using comparatively small amounts of helium because only a small, thermally isolated mirror area 18c within the mirror surface 18a is cooled with liquid helium which circulates through a tubing system 32 in a known manner. In this system the surfaces 18a and 18c of the metallic mirror are separated from each other by thermoinsulation 33, and the helium cooling system is connected by, e.g., a tube 34 joining the two metal tanks 18b/18d and 21a. The very low temperature mirror area 18c is flushed with helium gas 35 through, for example, a feed line 36 that first passes through the liquid N$_2$ 19 and then transports the helium, via a valve 37 that at the same time is designed as swivel axis AA', into the hollow lid 38, which pivots around verticle axis AA'. The helium gas, which is placed under pressure slightly above atmospheric pressure, finally vents through the gap between the lid 38 and the mirror surface 18a and, due to the small width of this gap, prevents nitrogen gas from diffusing in from the chamber space even at low helium flow rates. Immediately before the specimen is placed on mirror area 18c, the lid is swung aside around axis AA' by mechanical or electrical means using a suitable triggering mechanism, for example, a photodiode. This causes the mirror area 18c to be accessible for cryofixation.

As shown in FIG. 3, a practical elaboration of the invented freezing chamber 7b consists in the fact that by means of metal deflectors 39, a portion 22c of the evaporating nitrogen is used for continuous nitrogen flushing of the freezing chamber 7b and that only the remainder 22d of the evaporating nitrogen is heated to room temperature by the thermostatically heated metal jacket 27 in the gap 23, in a manner similar to that shown in FIG. 2. In this case, if required, the amount of nitrogen gas 22c available for flushing can be considerably increased by the use of heating elements 39a.

Another elaboration of the invented system consists in the fact that the refilling mechanism connected to the phase separator 20 can be functionally switched so that the upper level sensor 29 is turned off and hence refilling continues until liquid $N_2$ overflows the upper rim of the side walls 18d, and in this way part of the freezing chamber fills with liquid $N_2$. This filling process may, for example, be continued automatically until the level of liquid nitrogen in the freezing chamber 7b reaches level sensor 30, which then shuts off the refilling system. In this way not only can injected specimens be thoroughly frozen in their entirety, but also preparations can be carried out under liquid $N_2$ at $-196°$ C.

Finally, as shown in FIG. 3, other elaborations of the invented freezing chamber may consist in the fact that the mirror area 18c in metal component 41 capable of being cooled with helium is outfitted with a temperature sensor 42a and a heating element 42b of minimal heating capacity to make it possible to measure the temperature attained at any given time or to evaporate rapidly condensates, for example, those of solid nitrogen, before closing the lid 38 for a new helium cooling cycle.

Figure 4A:
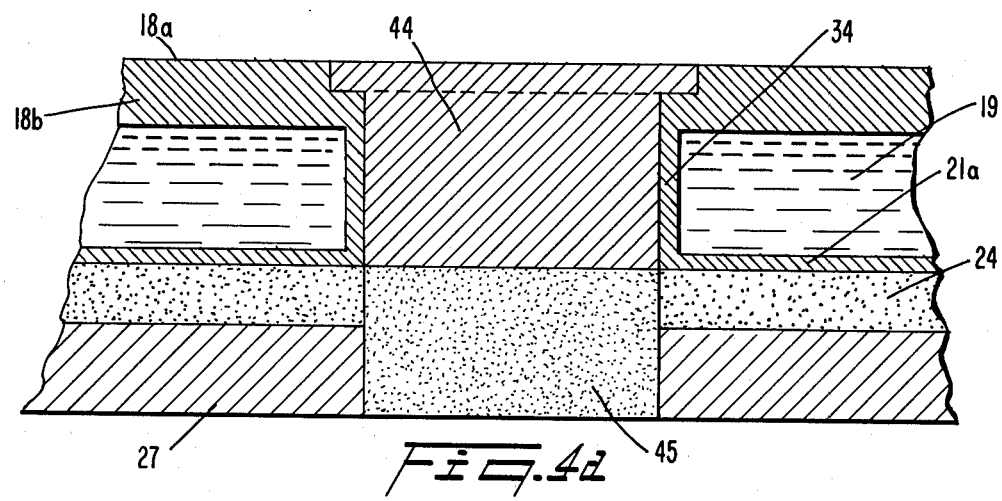
Figure 4B:
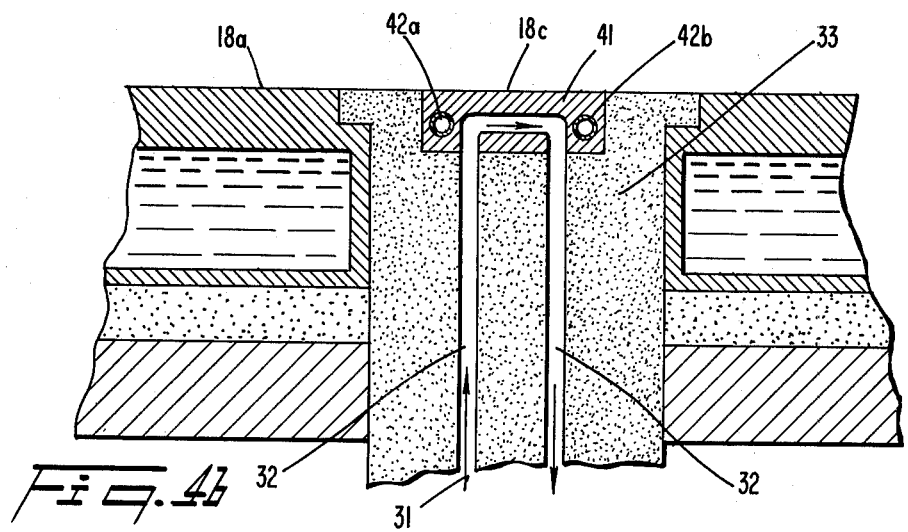
Figure 4C:
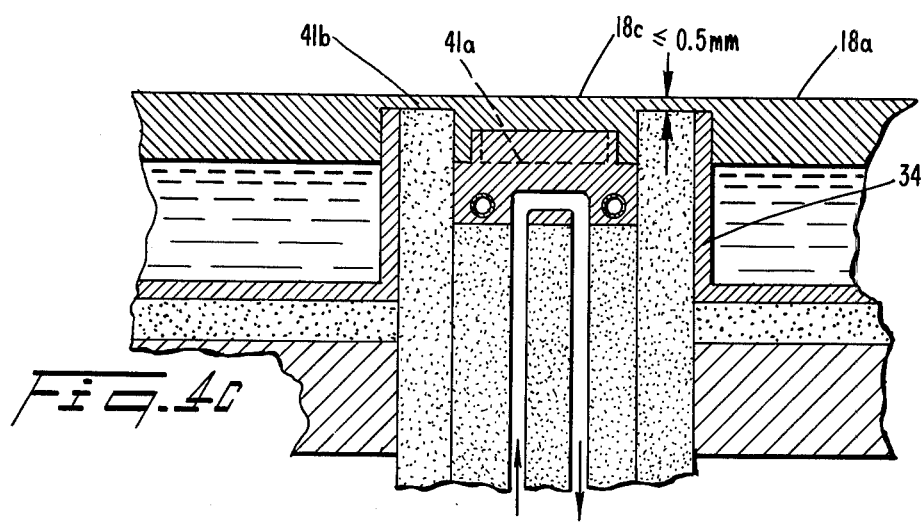
Figure 4D:
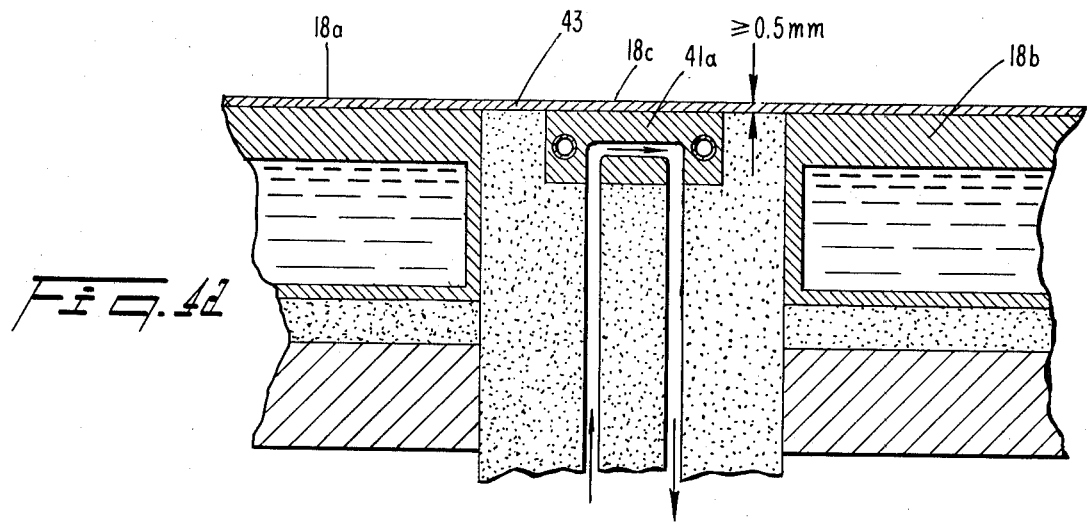
Figure 4E:
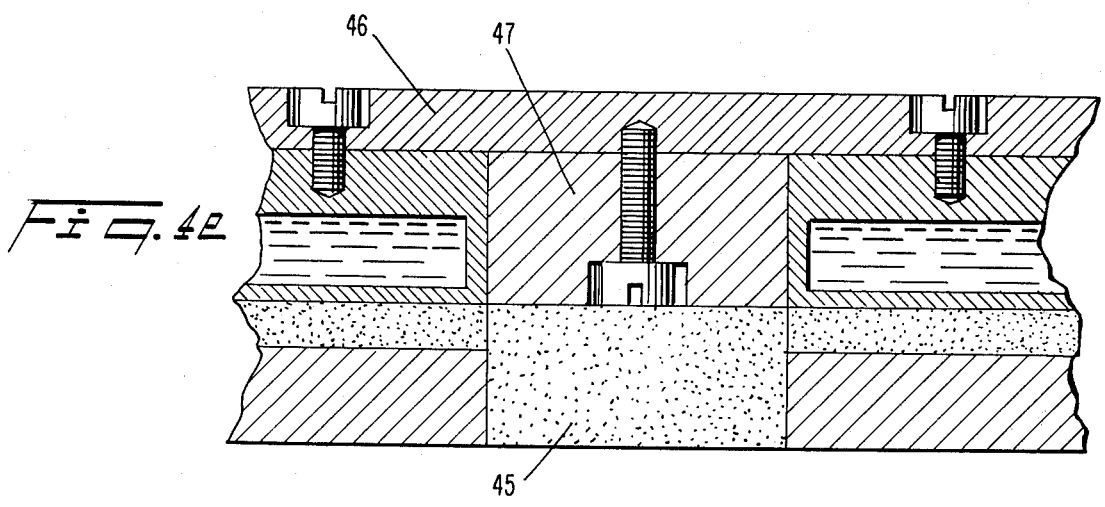
Figure 4F:
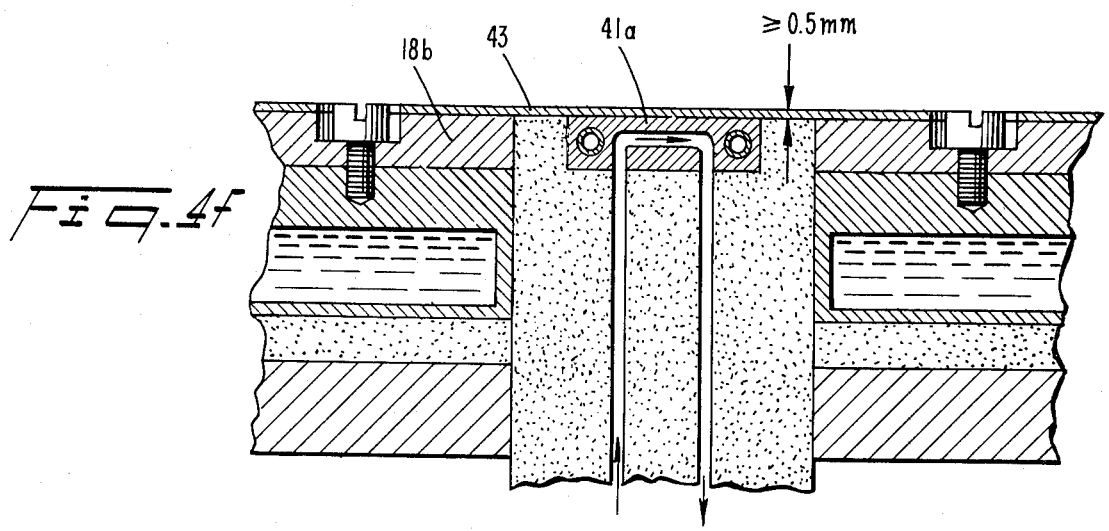

Within the scope of the invention, the device described in FIG. 3 may be realized in the most different variations and combinations. Thus, for example, as shown in FIG. 4, it is possible to separate the surface areas 18a and 18c of the metallic mirror or the metallic blocks 18b and 41 from each other by means of insulation 33 in various ways, wherein the metallic mirror surfaces of mirror areas 18a and 18c can be completely separated from each other (FIG. 4b) or can remain connected by a thin metallic layer 41b or 43 (FIGS. 4c, d, and f). Similarly, the mirror area 18c can be mounted directly on the part 41 through which helium circulates (FIG. 4b) or it may be placed in intimate thermal contact with a part 41b, through which helium circulates (FIGS. 4c, d, and f). Finally, the entire metallic mirror surface 18a/18c may consist of a continuous thin metal sheet 43, for example, 0.5 mm. thick, stainless, highly polished, specialty steel sheet (FIGS. 4d and f).

In a similar fashion, the freezing chamber may be equipped as appropriate for any given requirements with an optional helium supply by outfitting the standard model chamber with only an opening for receiving the tube 34; this opening is sealed by a metal stopper 44 and an insulating cylinder 45 (FIG. 4a) or by a continuous sheet metal sheathing 46 in conjunction with a metal cylinder 47 (FIG. 4e), so that components 45, 46, 47 may be exchanged for the helium cooled system (FIG. 4b or f) as required. Aside from these variations in the cooling surface, it is feasible to adapt the system for special applications by adding suitable electrical measuring instruments and switching devices; for example, photodiodes for triggering specific processes or coordinated operations and suitable connections for oscilloscopes. Moreover, for the character of the invention, it is immaterial in what manner the lid 38 swings aside and the specimen is placed on the metallic mirror. Thus, for example, the lid may swing aside around a horizontal axis instead of the vertical axis shown in FIG. 3, or the specimen may be introduced onto the mirror surface via a circular rather than the straight-line injection path. Furthermore, it is not important how the various preparation steps, for example, preparation of freshly sectioned planes, triggering of injection, and swinging aside the lid are effected, as well as which injectors are used for different solid or liquid specimens. Finally, it is also unimportant what type of cryogen supply, including all connections as well as the specific design of the refilling system, is used.

What is claimed is:

1. In a device for metallic mirror-cryofixation and subsequent cryopreparation of biological materials for microscopic, in particular electron microscopic, examinations having a freezing chamber, first cooling means for cooling said chamber with a first cryogen and a mirror surface mounted in said chamber for rapidly cooling a specimen placed in contact with said surface, the improvement comprising thermal insulation means to thermally isolate a portion of said mirror surface from the remainder of said mirror surface, cover means to form a small chamber in cooperation with said portion of said mirror surface, second cooling means for cooling said portion of said mirror surface with a second cryogen and the second cryogen having a lower liquid temperature than said first cryogen.

2. The improvement according to claim 1 characterized by the fact that the portion of said mirror surface (18c) has a surface area between 1 and 10 cm$^2$, can be cooled to $\leq 200°$ K., and the second cryogen is helium.

3. The improvement according to claim 2 characterized by the fact that the remainder of said mirror surface (18a) has a surface area of at least 50 cm$^2$ and can be cooled to a temperature of $\leq 100°$ K., preferably by means of liquid nitrogen.

4. The improvement according to claim 1 characterized by the fact that the cover means is a material having low heat capacity and low mass.

5. The improvement according to claim 1 characterized by the fact that said portion lies in the same horizontal plane as the remainder of the mirror surface.

* * * * *